(12) United States Patent
Berey et al.

(10) Patent No.: US 10,463,790 B2
(45) Date of Patent: Nov. 5, 2019

(54) STORAGE CASE WITH THE CAPABILITY OF COMMUNICATION AND MEDICAL DATA ACQUISITION

(71) Applicants: Attila Berey, Székesfehévár (HU); Péter Markovich, Budapest (HU); Béla Tímár, Budapest (HU)

(72) Inventors: Attila Berey, Székesfehévár (HU); Péter Markovich, Budapest (HU); Béla Tímár, Budapest (HU)

( * ) Notice: Subject to any disclaimer, the term of this patent is extended or adjusted under 35 U.S.C. 154(b) by 0 days.

(21) Appl. No.: 15/556,265

(22) PCT Filed: Mar. 7, 2016

(86) PCT No.: PCT/HU2016/050008
§ 371 (c)(1),
(2) Date: Sep. 6, 2017

(87) PCT Pub. No.: WO2016/142726
PCT Pub. Date: Sep. 15, 2016

(65) Prior Publication Data
US 2019/0001058 A1      Jan. 3, 2019

Related U.S. Application Data

(60) Provisional application No. 62/129,114, filed on Mar. 6, 2015.

(30) Foreign Application Priority Data

Mar. 6, 2015   (HU) ..................... 1500091

(51) Int. Cl.
*H04B 7/00*    (2006.01)
*A61M 5/172*   (2006.01)
(Continued)

(52) U.S. Cl.
CPC ......... *A61M 5/1723* (2013.01); *A61B 5/0022* (2013.01); *A61B 5/0024* (2013.01);
(Continued)

(58) Field of Classification Search
CPC ... A61B 5/0006; A61B 5/0008; A61B 5/0022; A61B 5/0024; A61B 5/14532;
(Continued)

(56) References Cited

U.S. PATENT DOCUMENTS

2003/0038047 A1* 2/2003 Sleva ................. A61B 5/0002
                                                    206/370
2014/0311227 A1* 10/2014 Koski ............... G01N 27/3273
                                                      73/61.41

FOREIGN PATENT DOCUMENTS

JP       2014050456 A     3/2014
WO       03017860 A1      3/2003
(Continued)

OTHER PUBLICATIONS

International Search Reporting in corresponding International Application No. PCT/HU2016/050008, dated Sep. 6, 2016, 3 pages.

*Primary Examiner* — Nhan T Le
(74) *Attorney, Agent, or Firm* — Fitch, Even, Tabin & Flannery LLP

(57) ABSTRACT

The invention relates to a medical data acquisition communication device (100), comprising a housing (100') and electronics (110) arranged within the housing (100'), the electronics comprising a power supply (111); a processor unit (115); a memory unit (116); at least one short-range communication device (117); at least one long-range communication device (119); and a user interface (120) including at least one trigger signal generating element (123).

(Continued)

A core of the invention is that the long range communication device is (i) configured for wired communication, or (ii) configured for GPRS-based GSM communication and also comprises a SIM card (118).

14 Claims, 3 Drawing Sheets

(51) Int. Cl.
*A61B 5/00* (2006.01)
*A61M 5/00* (2006.01)
*G16H 40/63* (2018.01)
*G06F 19/00* (2018.01)
*A61B 5/145* (2006.01)
*H04W 4/80* (2018.01)
*H04B 1/3816* (2015.01)

(52) U.S. Cl.
CPC ............ *A61M 5/003* (2013.01); *G16H 40/63* (2018.01); *A61B 5/0006* (2013.01); *A61B 5/0008* (2013.01); *A61B 5/14532* (2013.01); *A61M 2205/3306* (2013.01); *A61M 2205/3317* (2013.01); *A61M 2205/3553* (2013.01); *A61M 2205/3561* (2013.01); *A61M 2205/3569* (2013.01); *A61M 2205/502* (2013.01); *A61M 2205/52* (2013.01); *A61M 2205/581* (2013.01); *A61M 2205/582* (2013.01); *A61M 2205/584* (2013.01); *A61M 2205/587* (2013.01); *A61M 2230/201* (2013.01); *G06F 19/3418* (2013.01); *G06F 19/3468* (2013.01); *H04B 1/3816* (2013.01); *H04W 4/80* (2018.02)

(58) Field of Classification Search
CPC .. A61M 2205/3306; A61M 2205/3317; A61M 2205/3553; A61M 2205/3561; A61M 2205/3569; A61M 2205/502; A61M 2205/52; A61M 2205/584; A61M 2205/587; A61M 2230/201; A61M 5/003; A61M 5/1723; G16H 40/63
See application file for complete search history.

(56) References Cited

FOREIGN PATENT DOCUMENTS

| | | |
|---|---|---|
| WO | 2005046559 A2 | 5/2005 |
| WO | 2005110387 A2 | 11/2005 |

\* cited by examiner

STORAGE CASE WITH THE CAPABILITY OF COMMUNICATION AND MEDICAL DATA ACQUISITION

CROSS REFERENCE TO RELATED APPLICATIONS

This patent application is the national phase of PCT/HU2016/050008 filed Mar. 7, 2016, which claims the benefit of Hungarian Patent Application No. P1500091 filed Mar. 6, 2015 and U.S. Provisional Patent Application No. 62/129,114 filed Mar. 6, 2015.

TECHNICAL FIELD

The present invention relates, in one aspect thereof, to a domestic and/or portable medical data acquisition communication device, preferably a communication storage case, for use primarily with pen type drug delivery devices. The present invention also relates, in a further aspect thereof, to a method to operate said medical data acquisition communication device. The invention relates further to a kit comprising said communication device.

BACKGROUND

Wide-spread use of a medical device is substantially affected by its cost and complexity. This particularly applies to people living with diabetes, the significant masses of whom can generally be considered disadvantaged as to their financial potential, especially in developing countries. Consequently, a newly developed device will only become a device that could improve their health and comfort if said device is generally a low-cost device and can optionally be used for a relatively long period of time. Moreover, the great masses of people living with diabetes (except for those having type I diabetes) are of older age, belonging generally to the age-group of above fifty, and thus most of them are unable or hardly able to use and to learn how to use advanced technological means and the most modern devices, such as e.g. computers, tablets, smartphones, etc. Therefore, beyond the aforementioned considerations, a newly developed device should have the most simple configuration and design as far as practical usage is concerned, and it should also be a device that has—within the range of possibilities—the least possible number of function buttons. A device that is cheap and easy to use in everyday life can result in effective application even amongst people living under disadvantaged conditions, and a more effective improvement in their health condition can be observed for such a device.

International Publication Pamphlet No. WO 2005/046559 A2 discusses a kit for administering and monitoring the administration of a medicament, particularly insulin. The kit comprises a storage case for receiving the pen type insulin delivery device and further regular devices necessary for personal treatment of a diabetic patient, e.g. a blood glucose meter, the test strips, the lancer, the replaceable lancets for the lancer, an insulin pen (optionally a spare insulin pen, too), as well as spare needles for the insulin pen(s). The kit further comprises a cap mountable on the insulin pen, which emits a radio-frequency signal, optionally by RFID technique, when it is removed from the insulin pen. The radiofrequency signal is received by the blood glucose meter or an electronical device connected thereto that—optionally after performing computing and data processing steps—transmits data through wireless data communication to an external device that can be e.g. any of a cellphone, PDA, computer, wrist watch, pager or a printer. According to this solution, the blood glucose meter makes a proposal to the user as to the amount of insulin to be administered based on the measured value of the blood glucose level, data preset by the physician and data provided by the user, as well as optionally data related to the times and amounts of previous insulin administrations. Said proposal is displayed on the display of the blood glucose meter.

Said WO document contains no mention of the fact whether the communication storage case of said kit would be capable of GPRS-based data communication. Furthermore, in case of the solution discussed in said document, the storage case performs communication only to a minimal extent, and sending and receiving of data take place almost always only between the cap and the blood glucose meter. Or putting this another way, the case, in practice, serves merely for storage purposes.

However, a solution would be also advantageous, wherein the storage case that stores various tools could function as a communication center as well.

SUMMARY

An object of the present invention is to provide such a domestic and/or portable communication device that is configured—besides the function of storing various tools—to be capable of establishing data communication link(s) with said tools and, through the established communication link(s), reading out pieces of information available in said tools as to the health condition of the patient, wherein said pieces of information have been measured and/or stored by the tools themselves. A further object of the invention is to provide a method to operate such a domestic and/or portable medical data acquisition communication device.

In a further aspect, the aforementioned objects are achieved by providing a kit comprising the communication device according to the invention and at least one further device selected from the group of medical measuring devices and drug delivery devices.

On the one hand, a domestic and/or portable medical data acquisition communication device according to the invention, preferably the communication storage case is suitable for storing all the tools necessary for the personal therapy of a patient, e.g. in case of a person living with diabetes, an insulin delivery (dosing) device, several insulin cartridges, a blood glucose meter, test strips, a lancer and a lancet for the lancer, and optionally a spare insulin delivery device. This is a great help to a user, because in this way all the tools needed by her/him for testing/treatment are held at the same place, avoiding thereby her/his forgetting to keep one of the important tools with her/him, as well as the possibility of losing one of said tools.

On the other hand, the domestic and/or portable medical data acquisition communication device according to the invention, preferably a multifunction storage case is also equipped with electronics capable of communicating with the blood glucose meter, the insulin delivery device and optionally with further devices—amongst others, without completeness, e.g. a blood pressure meter, a personal scale, a pulse oximeter, a thermometer, an electrocardiography (ECG) instrument, a triglyceride or cholesterol level measuring device—, as well as sending and receiving medical data related to the patient during the communication. For example, in a preferred embodiment of the communication device according to the invention, the electronics integrated into the device, preferably into the communication storage case, copies and stores, preferably in its own memory unit, data provided by the blood glucose meter and further pieces of information as to the time and duration of administration (and thereby also the amount of insulin administered) provided by a data acquisition device mounted onto an insulin delivery device by means of data communication through a wireless data connection. Therefore, the size of the functional—i.e. data acquisition—elements/devices can be reduced, their appearance and corresponding usage can be optimized. Hence, considering the external appearance of the communication device, preferably the storage case, it represents a product that does not create the feeling of a medical product in the user and in her/his environment. Thus, its range of application widens. The wide spectrum of data acquired by the communication device according to the present invention, preferably the communication storage case, about the user for a given period of time can be processed and evaluated by e.g. the user's physician remotely through e.g. GPRS-based data communication. All this requires only that the patient use the device according to function.

Making use of the device is a great help in the life and work of both the user and the physician. Moreover, said usage requires only little effort from both parties, but as a result of the continuous control, it could considerably improve the life quality of the user.

In a preferred embodiment, the medical data acquisition communication device according to the invention, besides allowing to store and transport the insulin pen when it is not used, also allows to read out the pieces of information got stored electronically in said device during its usage regarding the insulin administration, e.g. data comprising the time of administration and the amount of insulin administered in a simple and reliable manner, and optionally requiring no active action from the user. Moreover, said device also allows then to make use of the thus obtained data—for the purpose of a later use—to derive and electronically store a personal database, i.e. a treatment log that corresponds to the user. The medical data acquisition communication device according to the invention, preferably the communication storage case is preferably also configured to transmit the treatment log for the purpose of a later use. Here, the term "later use" refers to—without completeness—the transmission and/or upload of the data contained in the treatment log into a data storage system of a physician or a hospital, as well as the assessment thereof by an expert and/or further use thereof to improve the quality of life of the patient living with diabetes.

BRIEF DESCRIPTION OF THE DRAWINGS

In what follows, the invention is discussed in detail with reference to the accompanying drawings, wherein FIGS. 1A and 1B schematically illustrate two exemplary arrangements of medical tools that can be disposed in a preferred embodiment of the medical data acquisition communication device according to the invention, provided in the form of a storage case.

DETAILED DESCRIPTION

Figure 1A:
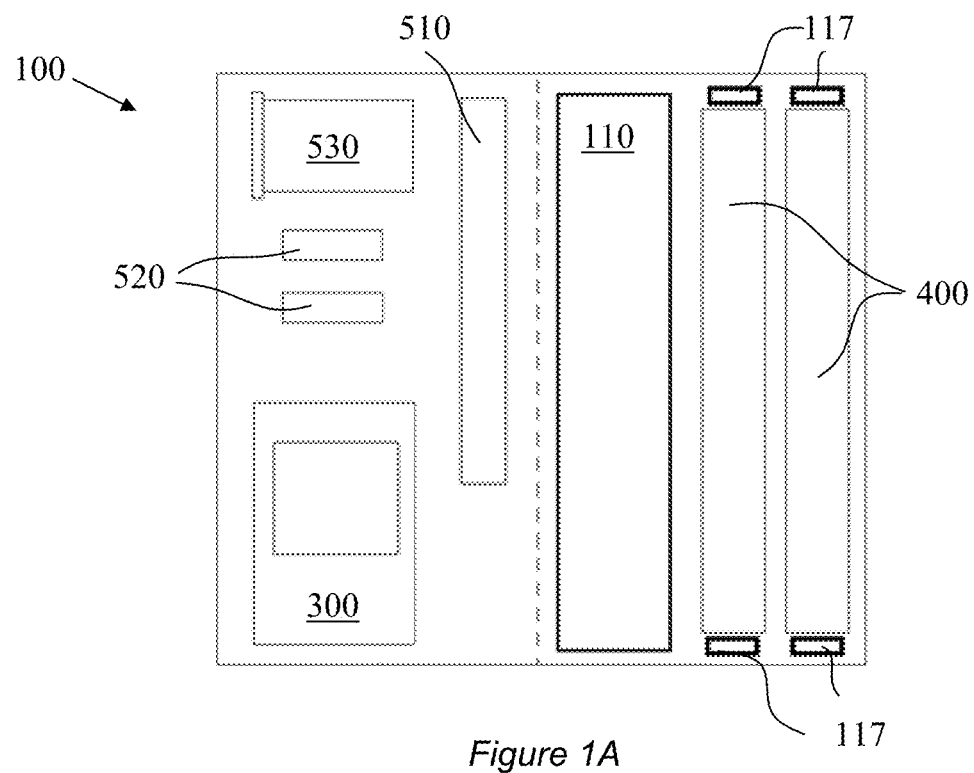
Figure 1B:
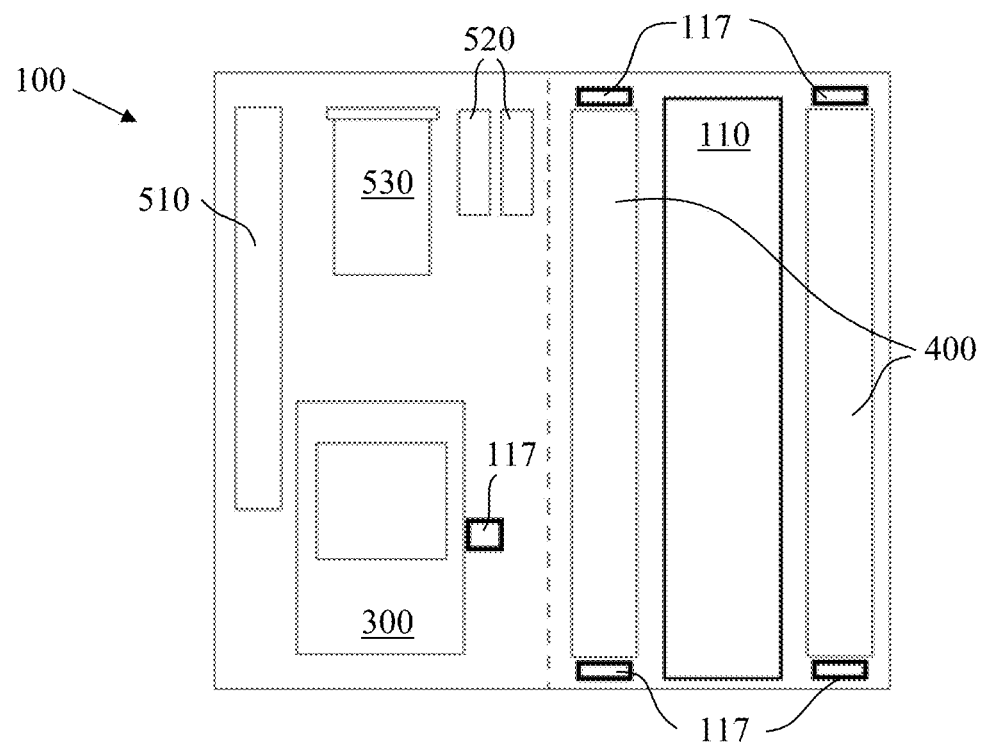

In the embodiments illustrated on FIGS. 1A and 1B, the allocation of internal space within the communication storage cases 100 representing preferred embodiments of the inventive medical data acquisition device accomplishes, besides that of the components of the electronics 110, a space-saving arrangement of the regularly used medical tools of a user, here specifically a diabetic patients (e.g. a blood glucose meter 300, insulin delivery (dosing) devices 400, i.e. insulin pens, a lancer 510, needles 520, test strips 530); thus making the medical data acquisition device simply and easily portable. Each of FIGS. 1A and 1B illustrates, furthermore, a possible arrangement of the short-range communication devices 117 forming part of the electronics that provides the (data)communication between the communication storage case 100 and the insulin pen 400 or the data acquisition device mounted on the insulin pen 400 in any orientation of the inserted insulin pen 400.

Figure 2:
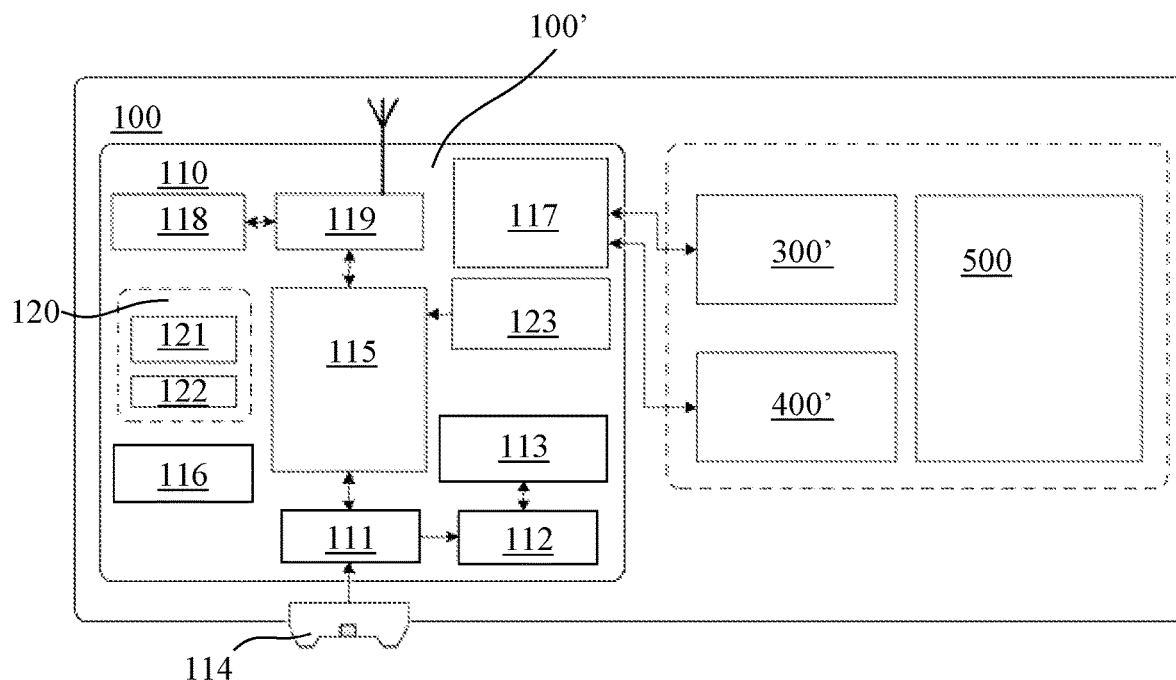
FIG. 2 schematically illustrates the connections amongst the components arranged fixedly within the storage case and the medical devices also disposed within said storage case representing here a preferred embodiment of the communication device according to the invention.

FIG. 2 schematically illustrates the arrangement of and the relative connections between various components in a communication storage case 100 representing a preferred embodiment of the medical data acquisition communication device according to the invention. The electronics 110, one or more medical measuring device(s) 300', preferably the blood glucose meter, one or more drug delivery device(s) 400', preferably the one or more insulin pen(s), and further non-electric accessories 500 (e.g. a lancer 510, needles 520 and/or test strips 530) are disposed in the housing 100' of the communication device. The electronics 110 may include a power supply 111, which is connected to an accumulator 113 through an accumulator management unit 112, wherein the accumulator 113 is preferably a lithium-ion accumulator, a power connector 114, preferably at least one micro-USB port, a processor unit 115, which is preferably a 16 bit, 32 MHz RISC processor having preferably a flash memory with the capacity of 128 kB, a memory unit 116, preferably a flash memory with the capacity 32 MB, short-range communication devices 117 communicating with the medical devices, said short-range communication devices preferably comprise wired, e.g. USB connections and wireless, e.g. NFC or Bluetooth interfaces, a SIM card 118, a long-range communication device 119, which is preferably configured to be capable of GPRS communication, an user interface 120, optionally comprising one or more LED(s) 121 configured to emit light of different colors, preferably a red LED and a green LED, a vibrator/speaker 122 and a trigger signal generating element 123, provided preferably in the form of a magnetometer or any other preferably magnetic-based proximity sensor. As is obvious for a person skilled in the art, the trigger signal generating element 123 can be any of a mechanical switch, a magnetic switch, a capacitive switch, an optical sensor, a magnetic sensor or any combination thereof.

Figure 3:
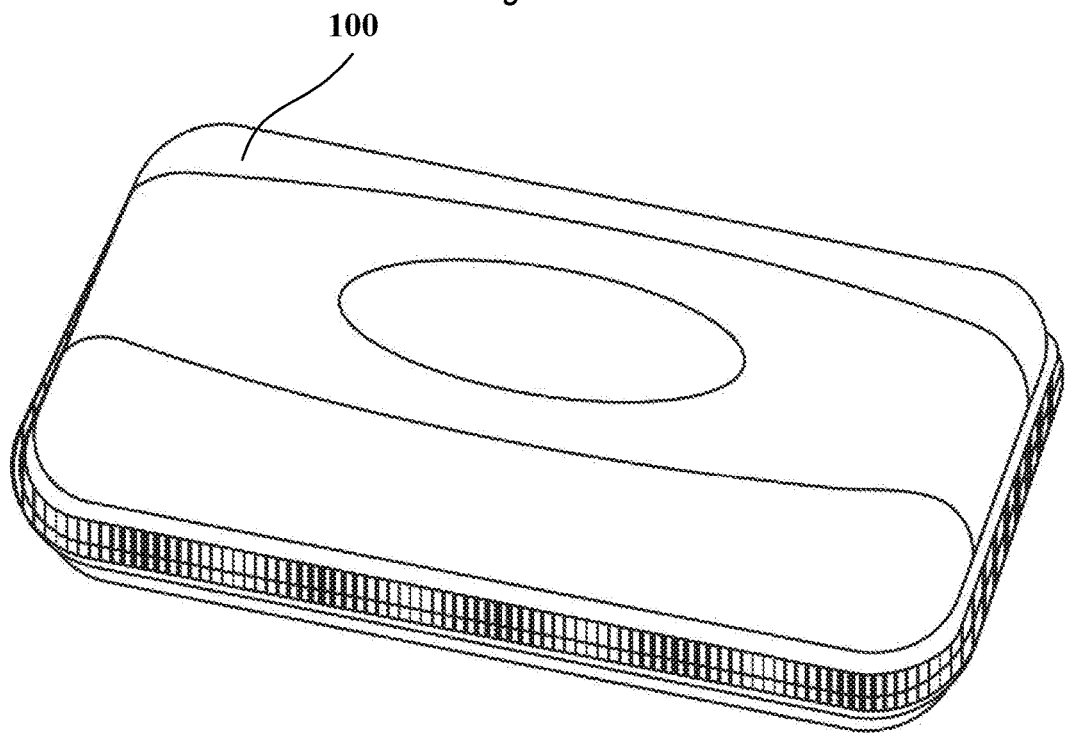
FIG. 3 shows the external appearance of a preferred embodiment of the communication device according to the invention, provided in the form of a storage case, in perspective view.

FIG. 3 illustrates a preferred external design of the communication storage case 100, which facilitates its practical usage and portability. The communication storage case 100 according to FIG. 3 can be closed and opened by means of a closing element, e.g. a zip fastener; however as is obvious to a person skilled in the art, various other closing elements can also be used (e.g. hook-and-loop fasteners or at least one snap fastener, etc.) equally advantageously to close the two half pieces of the communication storage case 100 together and thus to prevent dropping out of various tools arranged within the storage case. Ceasing to exist/forming of a closed state of the two half pieces of the communication storage case 100, that is, getting the closing element opened/closed, as well as the drawing-away/drawing-on of the two halves is monitored by the trigger signal generating element 123 discussed in relation to FIG. 2. When the half pieces come into a certain distance to one another, the trigger signal generating element 123 generates and transmits an electronic signal to the processor unit 115 in order to effect a wake-up (when closing is detected) or optionally a sleep (when opening is detected) of said electronics of the communication storage case 100. Based on the trigger signal, the processor unit 115 initiates establishing/breaking of the connections amongst the communication storage case 100 and the various medical measuring devices.

Figure 4:
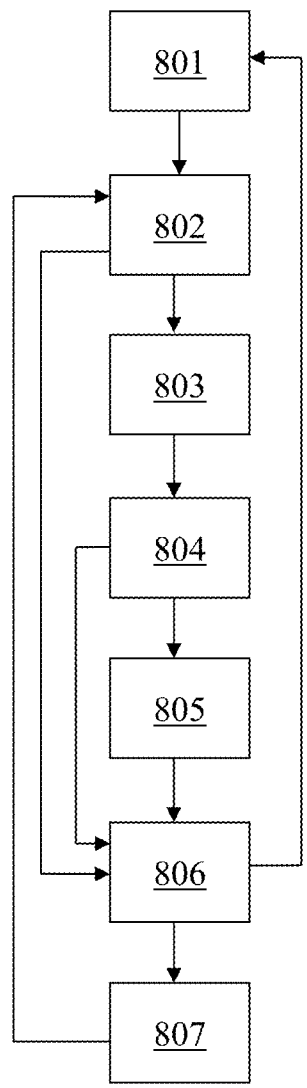
FIG. 4 is a flow chart showing operation of an exemplary embodiment of the communication device according to the invention in the form of a block diagram.

The block diagram in FIG. 4 illustrates a possible preferred variant of a method to operate the medical data acquisition communication device according to the invention. Accordingly, the device in its default (sleeping) mode (801) is waiting for a trigger signal; after receiving the trigger signal, it performs (802) data acquisition, wherein—in a state suitable for receiving incoming data—it is either further waiting or actively querying data from at least one further device, e.g. a blood glucose meter; upon detecting receipt of incoming data, the device receives and stores (803) the incoming data and reads out a device identification datum from the incoming data. Then the device compares (804) the received data with the data received previously from a device identified on the basis of said device identification datum. If, as a result of the comparison, the received incoming data are qualified as new data, the device stores the incoming data with the device identification datum in the memory unit, and initiates the transmission (805) of the incoming data with the device identification datum to at least one external database server. The targeted database server is selected in compliance with the type of data to be transmitted (i.e. blood glucose level, temperature, cholesterol level, etc.) and optionally by taking also into account the device identification datum. The device then performs a logic test (806) comprising determining whether or not the device is ready to return to the sleeping mode or a re-check is needed, which means a repeated execution of at least one of the steps 802 to 805. If re-check is needed, the device will be waiting (807) for a predetermined amount of time before it executes again at least one of the steps 802 to 805.

Data transmission (805) is performed preferably through a GPRS-based encrypted GSM data transmission channel. The data transmitted to the database server preferably include an identifier of the device being source of the data, the time of creation of the data (e.g. the time of insulin administration or blood glucose measurement) and at least one further datum (e.g. a measured blood glucose level, an amount of insulin administered or other measurement data obtained from the medical device).

The logic test (806) deems, for example, the re-check necessary if no re-check has been performed since receipt of the trigger signal (i.e. the steps 802 to 805 have been performed only once). Optionally, it also tests the condition whether or not at least one of steps 802 to 805 has been successfully performed.

A waiting time before the repeated execution of steps 802 to 805 is preferably 3 minutes. The waiting time and the repeated execution of steps 802 to 805 serve to check if the user has finished every action related to the insulin administration.

The trigger signal may be generated by a mechanical switch, a magnetic switch, a capacitive switch, an optical sensor, an electric sensor or a magnetic sensor built into the device, preferably a magnetic sensor, in particular a magnetometer that detects closure of the storage case, and then it transmits a trigger signal to the processor unit. The advantage of the magnetic sensor against any other types of sensors/switches is the reliable detection of the shut of the storage case, the preventability of false activations due to external disturbances, e.g. vibration/impact, as well as its low consumption and passivity—i.e. its operation requires no intervention from the user.

The user interface of the communication device, optionally the storage case, contains the least possible number of elements, thereby minimizing the chance of failure and reducing the possibility of an erroneous user-intervention. Moreover, it allows a user-intervention-free and completely automatic operation. Certain functions of said storage case can optionally be controlled/set through a web based interface.

A preferred exemplary embodiment of the medical data acquisition communication device according to the invention is configured as a storage case, and all the therapeutic devices and the accessories thereof (preferably at least 2 pieces of insulin delivery pens, at least one piece of insulin cartridge, 1 piece of blood glucose meter, 1 box of test strips, 1 piece of lancer, about 1 to 5 pieces of lancets for said lancer and 1 or 2 needles mountable onto the insulin pens) are also stored in the case in an ordered and secured manner. Beyond its basic storage function, the storage case, naturally, could be suitable or adapted for storing other additional elements, too.

The medical data acquisition communication device according to the invention, preferably the communication storage case, comprises a built-in unit that reads out data stored in the blood glucose meter and/or in the data acquisition device mountable onto the insulin delivery device and/or in further medical measuring and/or treatment devices. The communication device, preferably the case comprises wired and/or wireless short-range communication devices 117, e.g. an USB port, a radio-frequency transceiver, infrared, Bluetooth, wifi, NFC ('near field communication') means, preferably Bluetooth and/or NFC, suitable for communicating with said devices, and thus is compatible and can be used without any modifications with medical devices currently in use. Compared to the currently used solutions, wherein one or more medical devices, e.g. the blood glucose meter and/or the insulin pen, are provided by a smart (intelligent) device and thus the acquisition and replacement thereof are especially costly, the present particular solution offers a highly cost-efficient solution. In particular, the 'smart' device (i.e. the storage case) adapted to communicate with 'dumb' devices makes the inventive system a lot more flexible and cost-efficient.

Furthermore, the medical data acquisition communication device according to the invention, preferably the communication storage case, also comprises a communication unit that is suitable for transmitting the read-out data, as well as for wired or wireless communications, in particular GPRS communication; the data communication with one or more external databases servers is performed through a wireless, in particular a GPRS-based encrypted GSM data transmission link.

The medical data acquisition communication device according to the invention, preferably the communication storage case, has a power supply, optionally a built-in accumulator that provides power for its functioning. Making use of a built-in accumulator instead of the wide-spread solution of non-rechargeable replaceable batteries for power supply serves the purpose of reducing environmental pollution. To charge the accumulator, the storage case is connectable to the electric mains. As is obvious to a person skilled in the art, a stand-alone version of the inventive device does not require internal energy storage devices (battery or accumulator), power supply can take place directly from the electric mains.

The medical data acquisition communication storage case according to the invention is preferably provided with a connector unit that can electrically charge the accumulator of the blood glucose meter (if it is necessary).

As far as the shape and material of the storage case is concerned, the case preferably is easy to handle, takes up little space (i.e. its external dimensions are relatively small) and has an appealing appearance. Accordingly, the communication device according to the invention, preferably the case itself, can be used in a simple manner, can be easily transported and its material requirements are low when it is about its manufacturing. Optionally, the storage case itself may be made of recyclable materials.

EXAMPLE

The medical data acquisition communication device according to the invention, preferably the communication storage case serves two purposes at the same time: firstly, it contains the electronics for data acquisition (from the blood glucose meter and the insulin delivery (dosing) devices) and data transmission (GPRS communication), and comprises an accumulator and a charger unit. Secondly, it stores the tools for daily usage of a person living with diabetes, i.e. 2 pieces of insulin pens, spare needles for the pens, a lancer, sterilized lancets, test strips, and blood glucose meter. The electronics collect data from the measuring devices and from the data acquisition device that is mountable to the insulin pen, then transmits the data to a server by GPRS communication, optionally in an automated manner. This requires no user-interaction. Part of the communication storage case containing the electronics takes up as little space as possible. Furthermore, the external dimensions of the communication storage case according to the invention are optimized in compliance with the devices to be stored in said case, as is clear e.g. in view of the space allocations applied in the preferred exemplary embodiments shown in FIGS. 1A and 1B. As a result of the optimized configuration/space allocation, the case in its entirety is relatively small, its external dimensions are preferably about 120 mm×190 mm×50 mm, thus the patient can keep it with him/her (as it fits in a larger pocket).

The electronics are arranged so that the individual elements take up as little space as possible, be connected suitably to each other (in a reliable and load resisting manner), the connecting wires shall not be susceptible to damage. Moreover, the design enables simple manufacturing and easy replacement of the SIM card required for GPRS communication and of the accumulator. Furthermore, the technical design fully matches with the external appearance of the storage case.

Due to complex processes (insulin administration, measurement), both an ergonomic design and a suitable selection of materials are essential. Due to multiple uses per day, durability and reliability are also essential.

The invention claimed is:
1. A method to operate a medical data acquisition communication device (100) for storing tools necessary for personal therapy of a patient and establishing data communication with one or more of said tools, the device (100) comprising:
   a housing (100'); and
   electronics (110) arranged within the housing (100'), the electronics comprising:
      a power supply (111),
      a processor unit (115),
      a memory unit (116),
      at least one short-range communication device (117),
      at least one long-range communication device (119) configured for any of wired communication and GPRS-based GSM communication, and
      a user interface (120) including at least one trigger signal generating element (123);
   said device (100) having a sleeping mode, the method comprising:
   performing by said device (100) steps of:
      waiting (801) in the sleeping mode for a trigger signal generated by the trigger signal generating element (123);
      performing (802) data acquisition in response to receiving the trigger signal; and
      receiving and storing (803) incoming data in response to detecting receipt of incoming data;
      reading out a device identification datum from the incoming data; and
      comparing (804) the received incoming data with data received previously from a device identified based on said device identification datum; and
      if, as a result of the comparison, the received incoming data are qualified as new data, storing the incoming data with the device identification datum in the memory unit, and initiating an automatic, user-intervention-free transmission (805) of the incoming data with the device identification datum to at least one external database server.

2. The method according to claim 1, further comprising selecting said targeted database server in compliance with a type of data to be transmitted.

3. The method according to claim 2, further comprising selecting said targeted database server in compliance with the type of data to be transmitted and the device identification data.

4. The method according to claim 1, further comprising receiving by the housing (100') at least one further item selected from a group comprising medical measuring devices (300'), drug delivery devices (400'), lancets (510), injection needles (520), and blood glucose test strips (530).

5. The method according to claim 4, wherein said medical measuring device (300') is a blood glucose meter (300) and said drug delivery device (400') is an insulin pen (400).

6. The method according to claim 1, further comprising using said communication device (100) in cooperation with commercially available medical measuring devices (300') and/or drug delivery devices (400') without any modification of said devices.

7. The method according to claim 1, wherein the at least one trigger signal generating element (123) is selected from a group comprising mechanical switches, magnetic switches, capacitive switches, optical sensors, electrical sensors, magnetic sensors, and any combinations thereof.

8. The method according to claim 7, wherein the housing (100') comprises a first half piece, a second half piece, and a closing element, and the method further comprising the closing element closing the first half piece and the second half piece together and opening the first half piece and the second half piece.

9. The method according to claim 8, further comprising the trigger signal generating element (123) generating and transmitting an electronic trigger signal to the processor unit (115) to effect a wake-up or a sleep of the electronics (110) in response to the first half piece having a certain distance from the second half piece.

10. The method according to claim 9, further comprising the processor unit (115) establishing and/or breaking the connection between the communication device (100) and the at least one further device in response to the trigger signal.

11. The method according to claim 1, further comprising selecting at least one device from a group comprising medical measuring devices (300') and drug delivery devices (400').

12. The method according to claim 11, further comprising controlling by the communication device (100) data communication between the communication device (100) and the at least one device.

13. The method according to claim 12, further comprising configuring said data communication between the communication device (100) and the at least one device as a two-way communication.

14. The method according to claim 13, further comprising adapting the communication device (100) to any one or combination of passively receiving data from the drug delivery device (400'), actively sending data to the drug delivery device (400'), and issuing instructions for altering operational parameters.

* * * * *